United States Patent
Agnihotri

(10) Patent No.: US 12,357,288 B2
(45) Date of Patent: Jul. 15, 2025

(54) ACCESS SITE MANAGEMENT SYSTEM FOR PERCUTANEOUS VASCULAR ACCESS

(71) Applicant: xDot Medical Inc., Maple Grove, MN (US)

(72) Inventor: Aashiish Agnihotri, Maple Grove, MN (US)

(73) Assignee: xDot Medical Inc., Maple Grove, MN (US)

( * ) Notice: Subject to any disclaimer, the term of this patent is extended or adjusted under 35 U.S.C. 154(b) by 0 days.

(21) Appl. No.: 18/667,084

(22) Filed: May 17, 2024

(65) Prior Publication Data

US 2024/0299019 A1    Sep. 12, 2024

Related U.S. Application Data

(63) Continuation of application No. 17/811,359, filed on Jul. 8, 2022, now Pat. No. 11,998,182, which is a continuation of application No. 17/457,169, filed on Dec. 1, 2021, now Pat. No. 11,382,609.

(60) Provisional application No. 63/120,795, filed on Dec. 3, 2020.

(51) Int. Cl.
*A61B 17/00* (2006.01)
*A61B 17/04* (2006.01)

(52) U.S. Cl.
CPC ...... *A61B 17/0057* (2013.01); *A61B 17/0401* (2013.01); *A61B 2017/00663* (2013.01); *A61B 2017/00867* (2013.01); *A61B 2017/0496* (2013.01)

(58) Field of Classification Search
CPC .............. A61B 2017/00663; A61B 2017/0496
See application file for complete search history.

(56) References Cited

U.S. PATENT DOCUMENTS

| | | | |
|---|---|---|---|
| 5,496,332 A | 3/1996 | Sierra et al. | |
| 5,836,955 A | 11/1998 | Buelna et al. | |
| 6,464,707 B1 | 10/2002 | Bjerken | |
| 10,765,418 B2 | 9/2020 | Foerster | |
| 11,998,182 B2 * | 6/2024 | Agnihotri | A61B 17/0466 |
| 2008/0097480 A1 | 4/2008 | Schorr et al. | |
| 2009/0299409 A1 | 12/2009 | Coe et al. | |
| 2010/0256679 A1 | 10/2010 | Ducharme | |
| 2010/0262166 A1 * | 10/2010 | Boraiah | A61B 17/34 606/232 |
| 2010/0305609 A1 | 12/2010 | Cartledge et al. | |
| 2012/0010470 A1 | 1/2012 | Ducharme et al. | |
| 2012/0071903 A1 | 3/2012 | Knoell | |

(Continued)

OTHER PUBLICATIONS

International Search Report and Written Opinion mailed Aug. 23, 2023 for Application No. PCT/US2023/024275 (9 pp).

*Primary Examiner* — Alexander J Orkin
(74) *Attorney, Agent, or Firm* — Fox Rothschild LLP

(57) ABSTRACT

The disclosure provides a dynamic vascular access and closure device for radial cinching of an access site. The device includes a tensioning tube, a resilient member disposed within the tensioning tube, and a plurality of sutures extending axially between a distal end of the tensioning tube and a proximal end of the tensioning tube. A proximal end of each of the plurality of sutures can be configured to attach to the resilient member such that movement of that suture causes compression or extension of the resilient member within the tensioning tube to provide cinching to the sutures.

13 Claims, 12 Drawing Sheets

(56) References Cited

U.S. PATENT DOCUMENTS

| | | |
|---|---|---|
| 2012/0191133 A1 | 7/2012 | Ferree |
| 2014/0354808 A1 | 12/2014 | Hansen |
| 2015/0080902 A1 | 3/2015 | Jaramillo et al. |
| 2017/0086807 A1 | 3/2017 | Larzon et al. |
| 2018/0228478 A1 | 8/2018 | Fortson |
| 2019/0336116 A1 | 11/2019 | Walters et al. |
| 2022/0175356 A1 | 6/2022 | Agnihotri |

* cited by examiner

ACCESS SITE MANAGEMENT SYSTEM FOR PERCUTANEOUS VASCULAR ACCESS

CLAIM OF PRIORITY

This application is a continuation of and claims priority to U.S. patent application Ser. No. 17/811,359, filed Jul. 8, 2022 (now U.S. Pat. No. 11,998,182), which is a continuation of and claims priority to U.S. patent application Ser. No. 17/457,169 filed Dec. 1, 2021 (now U.S. Pat. No. 11,382,609), which claims priority to U.S. Provisional Appl. No. 63/120,795 filed on Dec. 3, 2020, the disclosures of each of the priority applications are incorporated herein by reference in their entireties.

FIELD OF THE DISCLOSURE

The present disclosure generally relates devices and methods for gaining percutaneous access to the lumen of a blood vessel and for subsequently closing the access site into the blood vessel.

BACKGROUND OF THE DISCLOSURE

Minimally-invasive, catheter-based interventions have in many ways revolutionized the treatment of vascular diseases. In many interventional procedures, an interventional device is introduced to the body through the patient's artery or vein (percutaneous approach). For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., a catheter) can pass through the sheath and to an operative position within the vascular system. While these procedures present various medical advantages, the potential for bleeding during the procedure can present dangers to the patient. As such, intravascular and intraluminal procedures unavoidably present the problem of stopping the bleeding at the percutaneous puncture after the procedure has been completed and after the instrument (and any insertion sheaths used therewith) has been removed.

Moreover, many such interventional processes often require multiple accesses to the blood vessel for which the percutaneous access site must remain open for long periods of time without excessive bleeding. Physicians may be required to manually prevent excessive bleeding during temporary closures, such as those occurring when changing catheters, dilators, or sheaths. Existing devices often do not provide access site management capabilities that prevent bleeding (e.g., during placement and removal of a vascular sheath) without manual intervention and/or do not facilitate multiple accesses into the vascular interior. Such devices may close an access site at the end of a procedure but require a new access site for later repeat access.

These problems are exacerbated when large bore access is required (e.g., in procedures such as transcatheter structural heart therapies (Transcatheter Aortic Valve Replacement (TAVR), Transcatheter Mitral Valve Replacement/Repair (TMVR/r) etc.), temporary mechanical circulatory support implantation (percutaneous Ventricle Assist Devices or pVADs), and percutaneous endovascular aortic abdominal aneurysm repair (PEVAR) where the size of catheters are typically in the range of 10-24 French or larger. Existing vascular closure devices are designed for small bore access, whereas many new interventional procedures require larger, more complex catheters. For this reason, some interventional procedures using larger catheters rely on a vessel cutdown to access the vein or artery. Using a surgical cutdown to access the blood vessel undermines the minimally-invasive aspect of the interventional procedure. Additionally, vessels of elderly patients are often heavily calcified, which can lead to closure difficulty and a high failure rate of conventional closure methods.

The current disclosure describes devices and methods directed towards solving some of the issues discussed above.

SUMMARY OF THE DISCLOSURE

Disclosed scenarios provide a dynamic vascular access and closure device and methods of use thereof.

For example, some of the disclosed scenarios include a dynamic vascular access and closure device for radial cinching comprising a tensioning tube that may include a resilient member disposed within the tensioning tube; and a plurality of sutures extending axially between a distal end of the tensioning tube and the proximal end of the tensioning tube. A proximal end of each of the plurality of sutures can be configured to attach to the resilient member such that movement of that suture causes compression or extension of the resilient member within the tensioning tube. The resilient member can comprise a spring.

The distal end of each of the plurality of sutures can be coupled to a vascular anchor. The vascular anchor can be a nitinol tube anchor (e.g., having three hooks) or a nitinol wire anchor.

The dynamic vascular access and closure device can further include a suture lock. In some embodiments, the sutures, vascular anchors, and suture lock can be a body-absorbable material. The vascular anchors can be nitinol anchors. In some implementations, the proximal end of each of the plurality of sutures may include a suture stop.

The dynamic vascular access and closure device can further include a resilient member stop within the tensioning tube (e.g., a step defined by a change in an internal diameter of the tensioning tube). Optionally, a force applicator may be disposed at a proximal end of the resilient member. The compression or extension of the resilient member against the resilient member stop can be the force applicator compressing the spring against the resilient member stop.

In some embodiments, at least one of the sutures can be configured to attach to a blood vessel and a distal end of the at least one suture can be configured to attach to the tensioning tube. In further embodiments, the resilient member can be configured to be in a first position to cause the plurality of sutures to cinch a vascular access site situated between the sutures when the sutures are attached to a blood vessel; or in a second position when the plurality of sutures are pulled to open the vascular access site, wherein a first length of the resilient member in the first position is greater than a second length of the resilient member in the second position.

Another scenario can include a dynamic vascular access and closure device including a plurality of sutures having a proximal end and a distal end, each of the plurality of sutures having a suture stop at the corresponding proximal end; a tensioning tube assembly comprising: a body having distal end and a proximal end, and a spring. The sutures can extend axially through the tensioning tube body and pulling of the sutures can cause application of pressure to the spring, via the suture stops. A tensioning of the plurality of sutures may be caused by opening of a vascular access site located between the plurality of sutures when the plurality of sutures are deployed to a blood vessel.

The distal end of each of the plurality of sutures may include a vascular anchor. The vascular anchor can be a nitinol tube anchor (e.g., having three hooks) or a nitinol wire anchor.

The suture stops may be knots placed in the proximal end of the sutures. The dynamic vascular access and closure device may further include a force applicator, which may be a hollow tube coaxial with the body of the tensioning tube and disposed at least partially inside the body of the tensioning tube such that a distal end of the force applicator contacts a proximal end of the spring. In some embodiments, the suture stops are disposed outside a proximal end of the force applicator. Optionally, a position of the force applicator with respect to the tensioning tube may be adjustable for increasing or decreasing pressure applied to the spring.

The dynamic vascular access and closure device may further include a suture lock. The suture lock can be disposed at the distal end of the tensioning tube and may be configured to be locked to the sutures while the sutures are under tension. The suture lock may be a ferrule configured to be crimped around the plurality of sutures. In other embodiments, the suture lock may be a semi-permanent suture lock.

Yet another scenario may include a dynamic vascular access and closure device for radial suture cinching including a plurality of vascular anchors configured for attachment to a blood vessel; a plurality of sutures having a proximal end and a distal end, the proximal ends having a suture stop and the distal ends being connected to the vascular anchors; a tensioning tube having a distal end and a proximal end, the distal end of the tensioning tube having a smaller diameter than the proximal end of the tensioning tube; and an inner biasing tube disposed at least partially inside the proximal end of the tensioning tube. The dynamic vascular access and closure device can further include a compression spring having a distal end and a proximal end, the spring being disposed inside the tensioning tube between the distal end of the tensioning tube and the inner biasing tube, wherein the distal end of the spring contacts a shoulder of the tensioning tube and the proximal end of the spring contacts the distal end of the biasing tube and a suture lock disposed between the distal end of the tensioning tube and the anchors. The sutures can extend axially through the tensioning tube, inner biasing tube, spring, and suture lock. The proximal end of the inner biasing tube can contact the suture stops. The inner biasing tube may be configured to transfer spring force from the compression spring to the plurality of sutures to cause opening or closing of a vascular access site located between the plurality of anchors when deployed on a blood vessel.

In various scenarios, methods of use of any of the dynamic vascular access and closure device can include deploying the plurality of sutures around the vascular access site (e.g., via the vascular anchors), inserting an interventional device into the vascular access site, and removing the interventional device from the vascular access site. Insertion of the interventional device into the vascular access site may cause tensioning of the plurality of sutures due to an increase in diameter of the vascular access site and compression of the compression spring. Removal of the of the interventional device can cause expansion of the compression spring and a dynamic closure of the vascular access site by cinching of the plurality of sutures.

BRIEF DESCRIPTION OF DISCLOSED EMBODIMENTS

Figure 1:
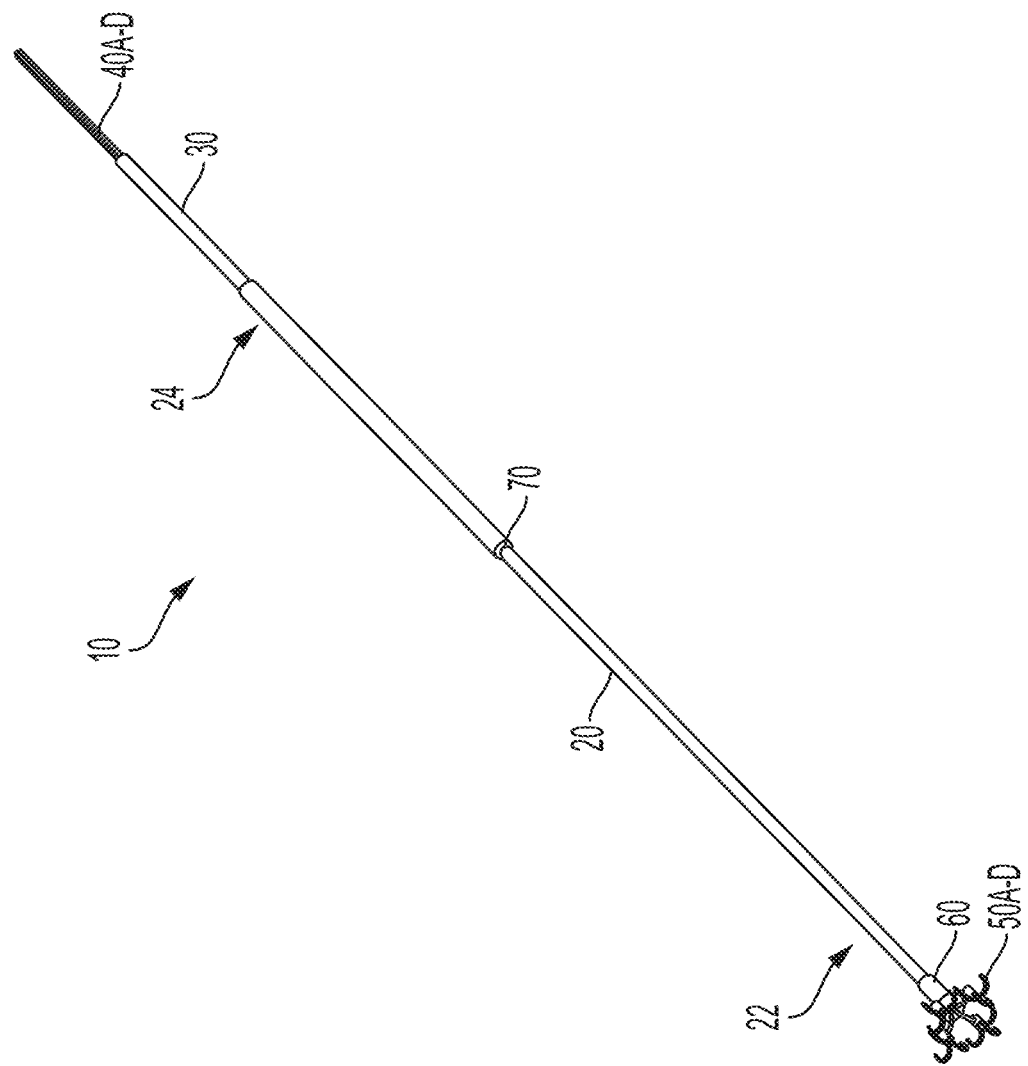
FIG. 1 is a perspective view of an example dynamic vascular access and closure device.

The devices and methods of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, proximal, distal, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". While the examples provided in this disclosure generally relate to percutaneous management of vascular access sites (i.e., in blood vessels), disclosed systems and methods may be used for other management of access sites, such as, but not limited to, access sites in various internal organs. For example, disclosed embodiments may be used for management of access sites to the heart (e.g., inside or outside of the heart) or the gastrointestinal tract.

Medical procedures may require access to the interior space of a blood vessel. This may be achieved using an interventional device such as a dilator or a catheter inserted through the wall of the vessel. In certain procedures, an interventional device may need to be removed temporarily and/or another interventional device may be need to be inserted. Because of the opening formed by an interventional device in the vessel wall, there is danger of bleeding when it is removed. Manual pinching of the vessel may be possible, but it requires the physician (and/or assistants) to pinch the vessel and before insertion of another interventional device, which may be difficult and still result in some blood loss. Then, the surgeon still must close the opening after the procedure is complete. Additional blood loss could result during the closure process. The devices and methods disclosed herein aim to improve upon at least one of the aforementioned problems. However, it shall be understood that the disclosure herein is not limited to merely solving these specific problems. Additionally, while the devices and techniques disclosed herein are described with respect to a human body or patient, it is understood that the devices and techniques may in suitable circumstances be applied to a non-human patient (i.e., in veterinary medicine).

In various implementations, the current disclosure describes a vessel access and closure device that places cinching sutures in the wall of a blood vessel and creates an access site through the wall of the blood vessel in the area bounded by the cinching suture. One or more interventional devices may be inserted directly through the access site or through an introducer sheath for performing an interventional procedure within the patient's vascular system. Once the interventional device is temporarily and/or permanently withdrawn, the cinching suture automatically tightens to close the access site into the vessel. A suture lock or a knot may, optionally, be used to lock the cinching suture once the interventional procedure has been completed and access to the vessel is no longer needed. The cinching suture also allows for repeated access to the blood vessel while minimizing, inhibiting and/or preventing substances flowing through the vessel opening during and/or after a procedure. The devices of this disclosure can, therefore, decrease resources (e.g., personnel time, materials, etc.) used to control or substantially eliminate bleeding/oozing/exuding fluids. The device can be applied by a wide range of individuals to quickly stem leakage and/or promote wound healing. Disclosed aspects may be employed percutaneously (i.e., without direct visualization of the user). However, it is understood that the devices and methods described herein can also be used under direct visualization by the user or with indirect visualization using, for example, a surgical endoscope.

In addition, the vascular access and closure device of this disclosure allows the use of a single device for providing access to the vessel lumen, irrespective of the diameter of the interventional device. Specifically, the embodiments of this disclosure can be used for interventional devices having a diameter of about 9 French to about 24 French. However, the disclosure is not limited to this range of sizes of interventional devices. In some embodiments, other sizes of interventional devices may be used. For example, devices of certain embodiments may work with size ranges of devices ranging from 12-24 French, 6-12 French, 9-24 French, as well as larger or smaller sizes. Although the devices are discussed in connection with promoting hemostasis, the devices and methods disclosed herein can be used in other applications to achieve different results, for example to provide management of access sites to the heart or gastrointestinal tract. For example, the anchors and sutures of the current access and closure device may be deployed proximate to and/or around an opening in the heart, and may be controlled as disclosed herein for providing access and hemostasis for such opening.

Referring now to the drawings, and in particular to FIGS. 1-5, an example dynamic vascular access and closure device 10 is shown and described. The dynamic vascular access and closure device 10 can be used to facilitate selectable access to the interior of a blood vessel in a body by permitting dynamic opening, closure, and reopening of an access site (e.g., a hole) in the vessel. As an example, suture anchors may be deployed around the access site in a vessel wall. Sutures connected to the suture anchors may be selectively tightened and relaxed to dynamically open and close the hole via a resilient member disposed within a tensioning tube, as discussed below. In various embodiments, the arrangement of suture anchors (once deployed around a vascular opening) may be configured to enable dynamic and automated radial cinching of a vascular opening by pulling the suture anchors in towards the center of the suture arrangement, where the vascular opening is located. For example, the suture anchors may be deployed in a circular manner around the vascular opening such that when the sutures are tensioned the suture anchors cinch together around the opening (like a purse string). Similarly, the suture anchors may be deployed in a manner that they form approximate vertices of a square, triangle, pentagon, hexagon, or the like with the vascular opening being at an approximate center of the arrangement. However, other arrangements are within the scope of this disclosure such as to allow for linear cinching, or the like.

As shown in the FIGS. 1-5, the dynamic vascular access and closure device 10 includes a tensioning tube 20 having a distal end 22 and a proximal end 24. The distal end 22 is the working end that is placed in proximity to a blood vessel. One or more suture filaments 40A-D (also, interchangeably referred to as suture wires and sutures) extend axially through the tensioning tube 20 between the distal end 22 and the proximal end 24, where a distal end of each suture wire is coupled to a suture anchor (suture anchors 50A-D). A resilient member 90 and a force applicator 30 are at least partially disposed within the tensioning tube 20.

As shown in the FIGS., the tensioning tube 20 includes an elongate, hollow, tubular outer shaft 201 which defines an inner lumen 202 within which other components can extend through or be placed. While tensioning tube 20 is illustrated as having a circular cross section, other cross sections, such as a square, rectangle, ellipse, etc. are also within the scope of this disclosure. The inner lumen 202 can include a first section 202(*a*) that has a smaller diameter compared to a second section 202(*b*). The smaller diameter of the first section 202(*a*) is large enough to allow the suture wires 40A-D to freely extend through it. The larger diameter of the second section 202(*b*) is large enough to house the resilient member 90 and the force applicator 30 (shown in FIG. 4A).

In various implementations, tensioning tube 20 can include a resilient member stop 70. The resilient member stop 70 can take a variety of forms, such as a step defined by a change in diameter of the tensioning tube from the larger lumen diameter to the smaller lumen diameter (as shown in FIG. 1), a gradual tapering of the tensioning tube 20 from the larger lumen diameter to the smaller lumen diameter, a pin or other structure extending through lumen 202 orthogonal to the main axis of the tensioning tube 20, or other suitable forms.

Tensioning tube 20 may be made from a variety of materials, such as polymers (e.g., plastics, rubber, etc.), metals or alloys (e.g., titanium, stainless steel), or any other suitable material with sufficient stiffness to prevent deformation under the compressive load applied by the tensioned sutures 40A-D.

A force applicator 30 may be an inner biasing tube that is at least partially disposed within the inner lumen 202 at the proximal end 24 of the tensioning tube 20 such that a distal end of the force applicator may reside inside the inner lumen 202 while a proximal end lies outside the inner lumen 202. In various implementations, the force applicator 30 may be a hollow tube. In various implementations, the force applicator 30 may be freely moveable with respect to the tensioning tube 20. While the force applicator 30 is shown as having a circular cross section, other cross sectional shapes can be used, such as a square, rectangle, ellipse, or others. The force applicator 30 and the tensioning tube 20 may have similar or different cross-sectional shapes. Force applicator 30 may also be made from a variety of materials, such as plastics or metals, with sufficient stiffness to prevent deformation under the compressive load applied by the tensioned sutures 40A-D.

A tubular resilient member 90 may be disposed within the tensioning tube 20 between the resilient member stop 70 and the distal end of the force applicator. In various implementations, the resilient member may be a coiled wire such as a spring and/or other types of resilient members that can be compressed against the resilient member stop 70, as discussed below in more detail. For example, the resilient member 90 may be an elastic tube or other structure capable of being repeatedly compressed and decompressed upon application of an axial force on one or both of its ends such as, without limitation, an air spring, hydraulic/gas spring, motor, or any now or hereafter known resilient members. As an example, resilient member 90 may be a linear actuator configured to tension sutures 40A-D. In such an example, the sutures 40A-D may be disposed around the perimeter of the actuator and through the force applicator member 30.

Optionally, the resilient member 90 may be replaced with a suture tensioning motor. In some such embodiments, a force applicator member 30 may not be needed. For example, the interior of tensioning tube 20 could include a motor with a shaft to which the sutures 40A-D could be connected. The shaft can turn to tension the sutures. The motor can be configured to apply a specific amount of torque that could effectively close the vascular opening, but also be overcome by an instrument (e.g., a dilator) separating the suture anchors and expanding the opening.

Figure 4A:
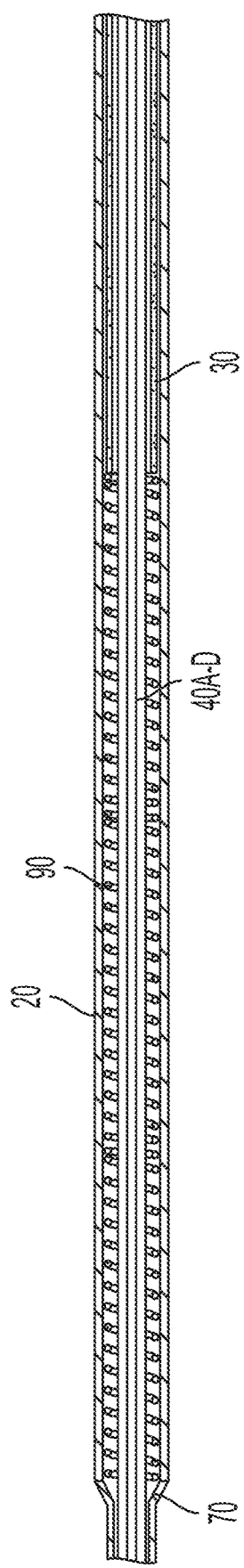
FIG. 4A is a cutaway view of the dynamic vascular access and closure device of FIG. 1 illustrating internals of the device.

FIG. 4A shows a cross-sectional cutaway view of the center of dynamic vascular access and closure device 10. This view illustrates sutures 40A-D extending axially through the length of the tensioning tube 20 and the force applicator 30. Resilient member 90 is disposed between the force applicator 30 and the resilient member stop 70. As illustrated in FIG. 4A, resilient member 90 may be a coil spring or a compression spring and the sutures 40A-D are configured to extend through the coil spring.

In some embodiments, force applicator member 30 may be a tube that also includes an inner step or taper defining a change in internal diameter of the tube (not shown here). The larger internal diameter may be disposed at the distal end of the force applicator member 30 and may be configured to fit around resilient member 90. For example, if resilient member 90 is a spring, the proximal end of the spring may fit inside a recess in the force applicator member 30. Such a configuration can help to reduce or eliminate potential binding of the spring between the tensioning tube 20 and the resilient member 90.

Figure 7:
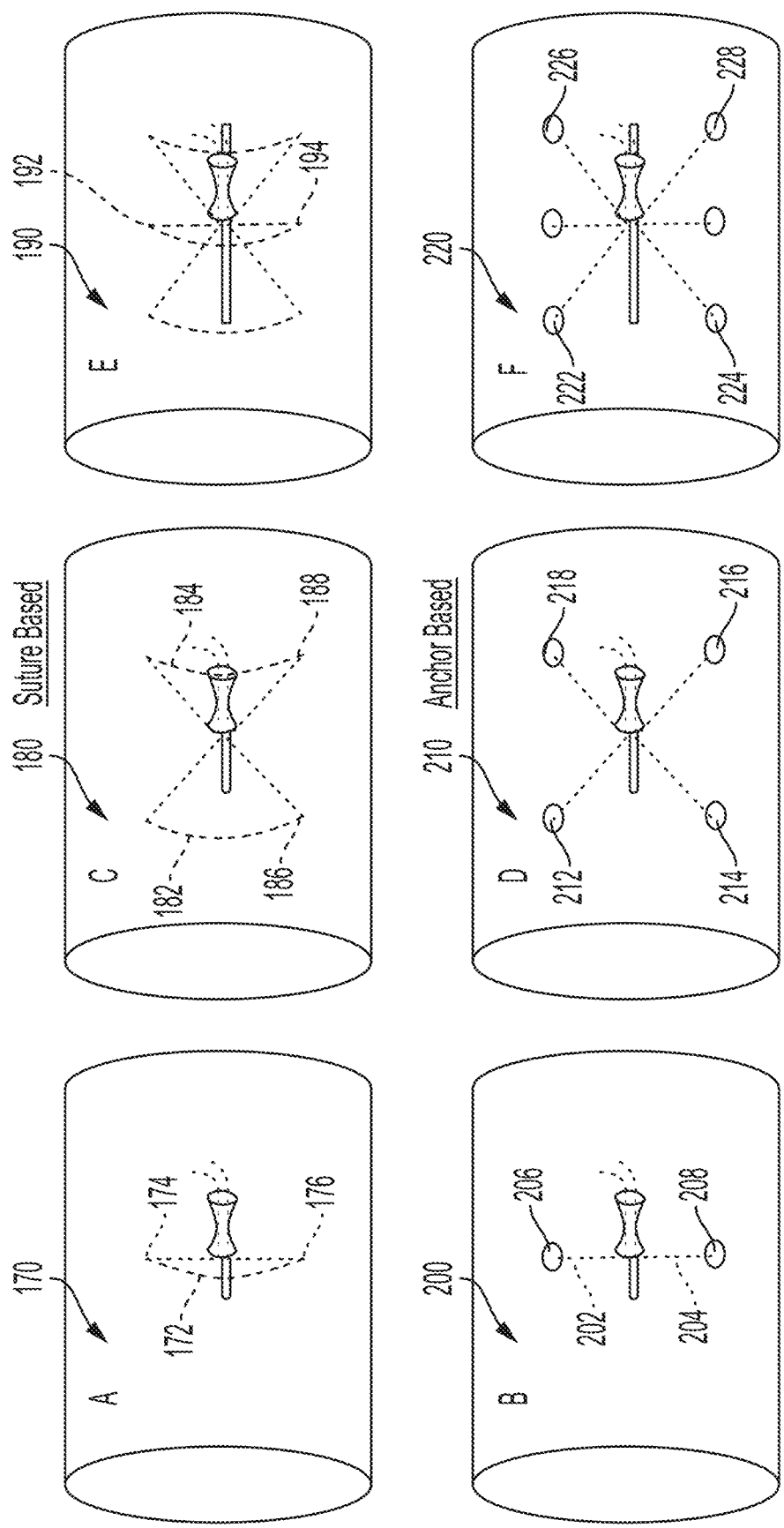
FIG. 7 illustrates various examples of suture placement configurations on a blood vessel wall.

As shown in the figures, suture filaments (or sutures) 40A-D can extend axially through the tensioning tube 20, the force applicator 30, and the resilient member 90. Sutures 40A-D can be monofilament or multifilament thread. A variety of materials can be used for sutures. Suture materials may generally be broken into two categories, absorbable (capable of being broken down and absorbed into the body) and non-absorbable (should be manually removed from the body). Suture materials include but are not limited to polyglycolic acid, polylactic acid (PLA), polypropylene, stainless steel, nylon, or others. While the Figures of the present disclosure illustrate four sutures, in various implementations, more or less sutures may be used depending, for example, on the diameter of the access site and/or an interventional device. For example, FIG. 7 illustrates exemplary embodiments having two, four, and six sutures. The number of sutures and suture anchors may depend on, for example, the size of the vascular access site (which may, in turn, depend on the size of the interventional device to be used). For example, 2 sutures may be used when the diameter of the interventional device is 6-12 French, 4 sutures may be used when the diameter of the interventional device is 12-24 French, and 6 sutures may be used when the diameter of the interventional device is higher than 24 French.

Figure 2:
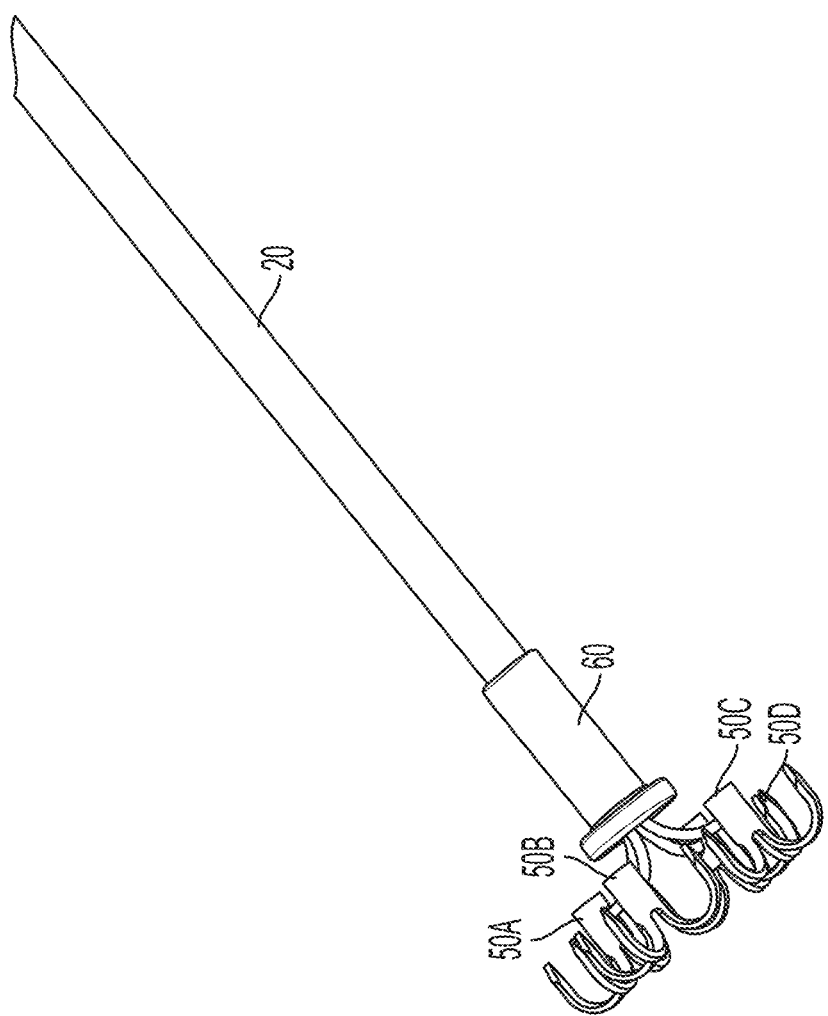
FIG. 2 is an enlarged view of a distal end of the dynamic vascular access and closure device of FIG. 1.

As shown in FIGS. 1 and 2, the distal end of each suture filament is coupled to a corresponding suture anchor 50A-D. Suture anchors 50A-D can be deployed in the surface of a blood vessel to attached the suture 40A-D to the surface of the vessel. Various forms of the suture anchors 50A-D are described below in more detail. Initially, the suture anchors 50A-D are configured to reside within a deployment device so that, as the insertion mechanism (e.g., needle tip) of a deployment device moves through a vessel wall in the distal direction (to create an access site or hole), the suture anchors 50A-D move smoothly forward and outside of the deployment device (without catching on the tissue). Once deployed, the suture anchors 50A-D open or spread, and anchor the distal end of the sutures 401A-D to the vessel wall. The deployment device leaves sutures 40A-D in the vessel wall, as it is withdrawn, anchored by the suture anchors 50A-D. It will be understood to those of skill in the art that any now or hereafter known deployment device can be used for deploying the suture anchors around an access site in a vessel wall. Furthermore, the sutures coupled to the suture anchors may be threaded through the tensioning tube of the device of this disclosure before and/or after deployment of the suture anchors.

In various implementations, a suture lock 60 may be provided for locking the sutures 40A-D upon permanent closure of a vascular access site (described below in more detail). FIG. 2 illustrates distal end 22 of dynamic vascular access and closure device 10 showing a close-up view of suture anchors 50A-D and suture lock 60. As shown in FIG. 2, the distal ends of sutures 40A-D may be fixed to one of suture anchors 50A-D. The suture anchors 50A-D may be deployed upon insertion into the vessel wall to provide a purchase for the suture in the vessel wall.

Suture anchors 50A-D can be made of super elastic or shape memory nitinol material wire(s) and/or tube(s). The nitinol tube(s)/wire(s) may be super-elastic and permit the anchors to assume a compressed state for insertion through the vascular wall without catching on or damaging the vascular wall. For example, the nitinol material wire(s) may be preformed by heat treating into a curvature, for example a hook shape, that will act as a suture anchor as shown in FIGS. 1 and 2. The curvature in the wire(s) can be straightened out by drawing it into deployment device. After the deployment device has advanced to the blood vessel wall, the wire(s) is advanced out and the curvature reforms to anchor the suture. Similarly, nitinol tubes may be laser cut into a hook shape and shape-set by heating the cut tube to a certain temperature. Then, the tubes can be pulled into their original tube shape into the deployment device, then return to their curved hook shape when removed from the deployment device. As an example, the hook formed suture anchors 50A-D of FIG. 2, may be collapsed into a small cylindrical folded shape when residing within the lumen of a deployment device. Optionally, the anchors may be disposed within removable sheaths that may be removed allowing the anchors to return to their hook shape. When the sutures are pulled from the outside of the vessel wall, the hooks will dig into the vessel wall and anchor the distal ends of the suture in the wall.

Figure 5A:
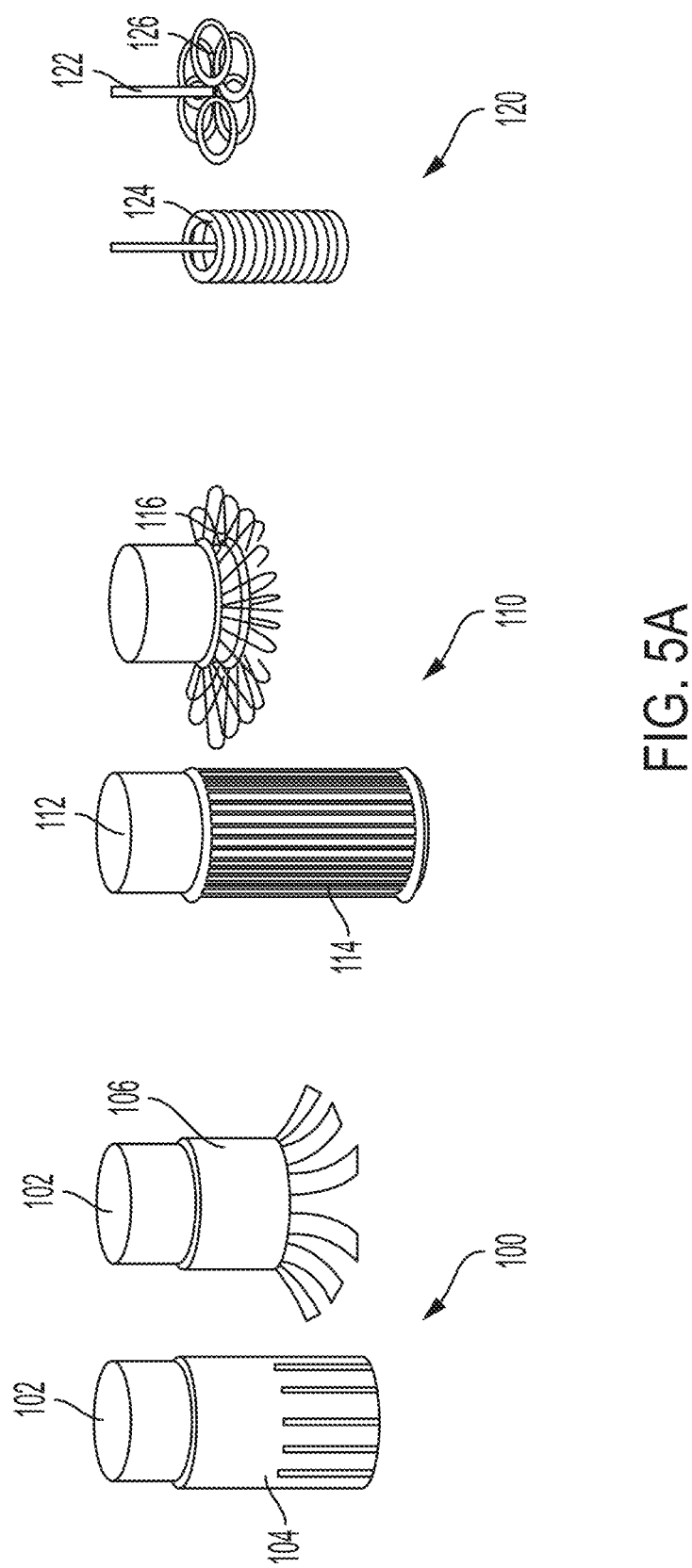
FIG. 5A illustrates various examples of vessel anchors.
Figure 5C:
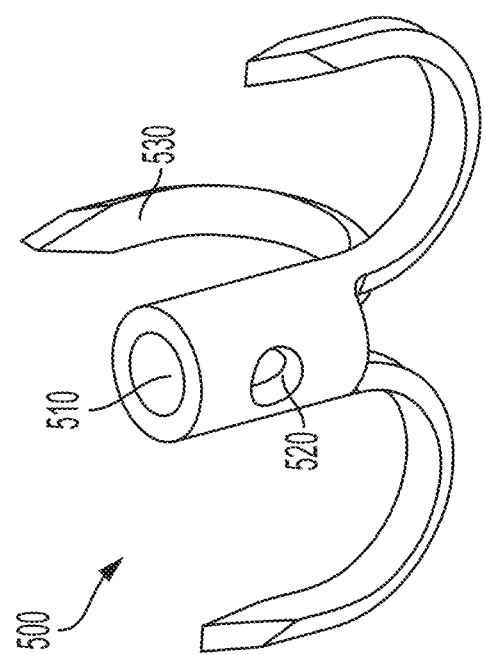
FIG. 5C illustrates an exemplary tube-based vessel anchor in a deployed configuration.
Figure 5B:
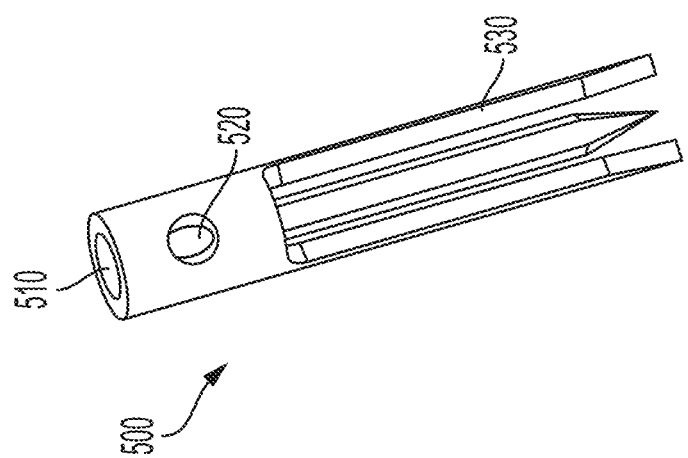
FIG. 5B illustrates an exemplary tube-based vessel anchor.

While the prongs or wires of anchors 50A-D in FIGS. 1-2 are illustrated with three prongs, anchors may have more or fewer prongs. Referring to FIG. 5A, various other types of suture anchors are possible, such as tube-based nitinol anchors 100, wire-based nitinol anchors 110 and suture knot anchors 120. Tube-based anchor 100 is illustrated at the end of suture 102. In a compressed or not expanded form 104, the anchor may be about the same diameter or slightly larger than the suture 102. When the anchor 102 is no longer compressed and is permitted to reach its expanded shape 106, the anchor may have a plurality of hooks or fingers that flare out and contact the interior vessel wall. Another example embodiment of a tube-based anchor is illustrated by FIGS. 5B and 5C, which show a three-prong laser cut tube-based anchor. As described above, a nitinol tube may be laser cut into a hook shape and shape-set by heating the cut tube to a certain temperature. Then, the tubes can be pulled into their original tube shape into the deployment device, then return to their curved hook shape when removed from the deployment device. Tube-based anchor 500 can include a tube body with a bore 510 running therethrough. Prongs 530 and/or hole 520 may be laser cut into the tube. Hole 520 can be used to attach a suture to tube-based anchor 500, as described above. For example, a knot or reflowed suture ball may prevent a suture run through 510 from pulling back through hole 520. After tube-based anchor 500 is cut, it may heat formed in to the hook shape illustrated in FIG. 5C. For example, prongs 530 may be formed into hooks that can engage with a vessel wall. Tube-based anchor may then be compressed (e.g., a shape such as that illustrated by FIG. 5B) inside a deployment device. When released from the deployment device, tube-based anchor 500 can return to deployed hook shape illustrated in FIG. 5C.

Referring back to FIG. 5A, similarly, wire-based anchor 110 may have a compressed form 114 (e.g., when it is inside a tube for deployment) and in an expanded form 116, have a variety of small wires that spring out and contact the vessel wall. Suture based anchors 120 may include a cylindrical knot of suture 124 that is inserted into the interior of the vessel. When the length of suture 122 is pulled on to the tension the suture 122, the knot 124 can be pulled into an expanded form 126, which can contact the interior of the vessel wall. While the anchors of FIG. 5 are described as either nitinol or suture-based anchors, anchors may be made from other suitable materials. Such vessel anchors can provide other advantages in addition to case of deployment and relative strength. For example, in elderly patients, the patient's vessels are often calcified, making it more difficult for traditional sutures to be placed across the vessel in a percutaneous manner. Disclosed vessel anchors may still penetrate the calcified vessel wall, permitting more simple vessel closure than would otherwise be possible without the anchors.

Though not illustrated in FIG. 5, other types of anchors are also possible, such as pledget-based anchors. Pledget-based anchors may include a suture that loops through the vessel wall and is tied or otherwise fixed to a pledget on the outside of the vessel wall. In this example, the pledget can serve both as a point for the suture to be affixed to and reinforcement for the vessel wall. In some embodiments, sutures 40A-D, anchors 50A-D, and suture lock 60 may be dissolvable inside the body of the patient. One or more of the sutures 40A-D, anchors 50A-D, and suture lock 60 may be constructed of a body-absorbable material (such as, but not limited to, PLA) that will break down inside the human body.

While the figures illustrate anchor-based sutures, the disclosure is not so limiting and non-anchor based sutures may similarly be used without deviating from the principles of this disclosure. Optionally, sutures 40A-D may not include an attachment device or anchor to a vessel wall (e.g., for use with older patients who have calcified/thicker vessel walls making it difficult for use of anchor-based sutures). Instead, the suture may be inserted into the vessel, extend through a portion of the interior space of the vessel, and exit at a different location on the vessel. Such an arrangement of non-anchor based suture attachments is also illustrated by FIG. 7 (e.g., as illustrated by suture attachment arrangements 170-190 in FIG. 7). In some embodiments, in which anchors are not used, the sutures may pass through the vessel and attach back to the tensioning tube.

Figure 3:
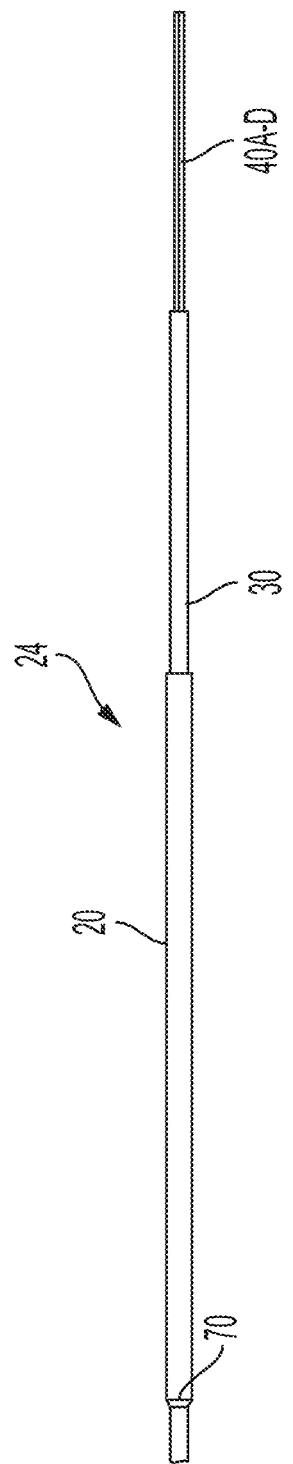
FIG. 3 is an enlarged view of a proximal end of the dynamic vascular access and closure device of FIG. 1.

The sutures 40A-D may also include a suture stop at or near the corresponding proximal ends. FIG. 3 illustrates the proximal end of 24 of the tensioning tube 20, with the proximal end of sutures 40A-D being exposed at the proximal end of force applicator member 30. A suture stop may take a variety of forms, including but not limited to, a knot tied in the sutures, a ferrule crimped onto the sutures, a reusable suture lock (such as that illustrated in FIG. 9), or other suitable alternative. Consistent with disclosed embodiments, the suture stop may be made of a variety of materials including suture material, plastics (e.g., PLA), titanium, etc. Optionally, a suture stop may also be an attachment and/or coupling to the tensioning tube body.

The suture stop is provided such that the length of the sutures 40A-D between the suture anchors 50A-D and the suture stop remains constant at all times. Furthermore, the suture stop is locked into a fixed position with respect to the resilient member 90 and/or the force applicator 30 such that the suture stop is configured to cause compression or release of the resilient member 90 between the force applicator 30 and the resilient member stop 70. When the sutures and suture anchors are initially inserted into a vessel access site, the resilient member 90 is in a semi-depressed state (and/or a resting state), and the access site is cinched closed by the sutures 40A-D (the length of the sutures 40A-D between the suture anchors 50A-D and the suture stop and/or the semi-depressed state of the resilient member is configured to cause the cinching). However, when an interventional device (e.g., a catheter, a dilator, a sheath etc.) is inserted through the access site, as the access site diameter increases, the sutures 40A-D are pulled apart and tensioned such that the suture stop causes further compression of the resilient member 90. In the tensioned state the sutures may cause the vessel membrane at the access site to close around the interventional device minimizing leakage during access to the vessel lumen, while the access site opening is expanded as needed to permit interventional device entry into the vessel lumen. As soon as the interventional device is removed from the access site, the access site diameter decreases and the kinetic energy stored in the depressed resilient member 90 is released causing the sutures 40A-D cinch the access site and the resilient member 90 moves back to its semi-depressed state (and/or resting state). As such, the vascular access and closure device 10 provides a dynamic vascular access via an access site that allows an interventional device to be repeatedly inserted to the access site while automatically closing the access site (temporarily and/or permanently) in the absence of the interventional device.

Figure 4B:
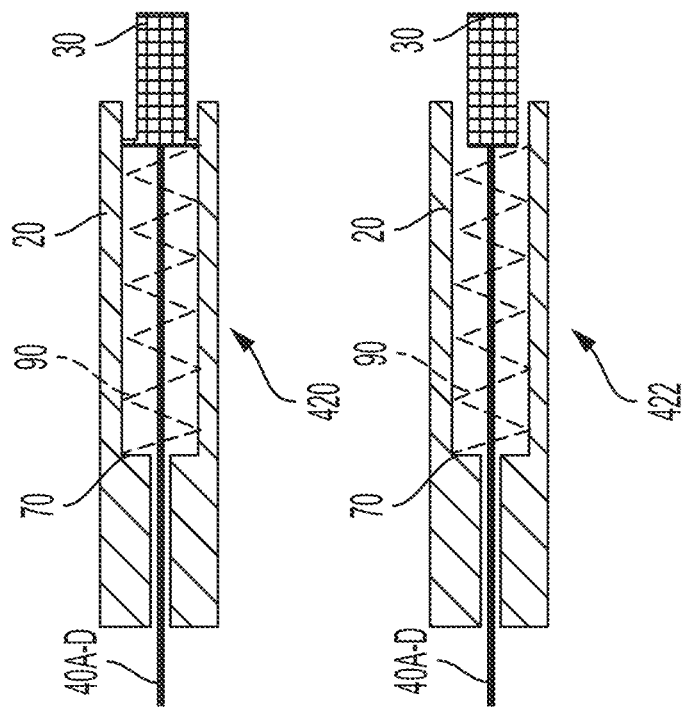
FIG. 4B illustrates cutaway views of alternative arrangements of a dynamic vascular access and closure device.
Figure 4B:
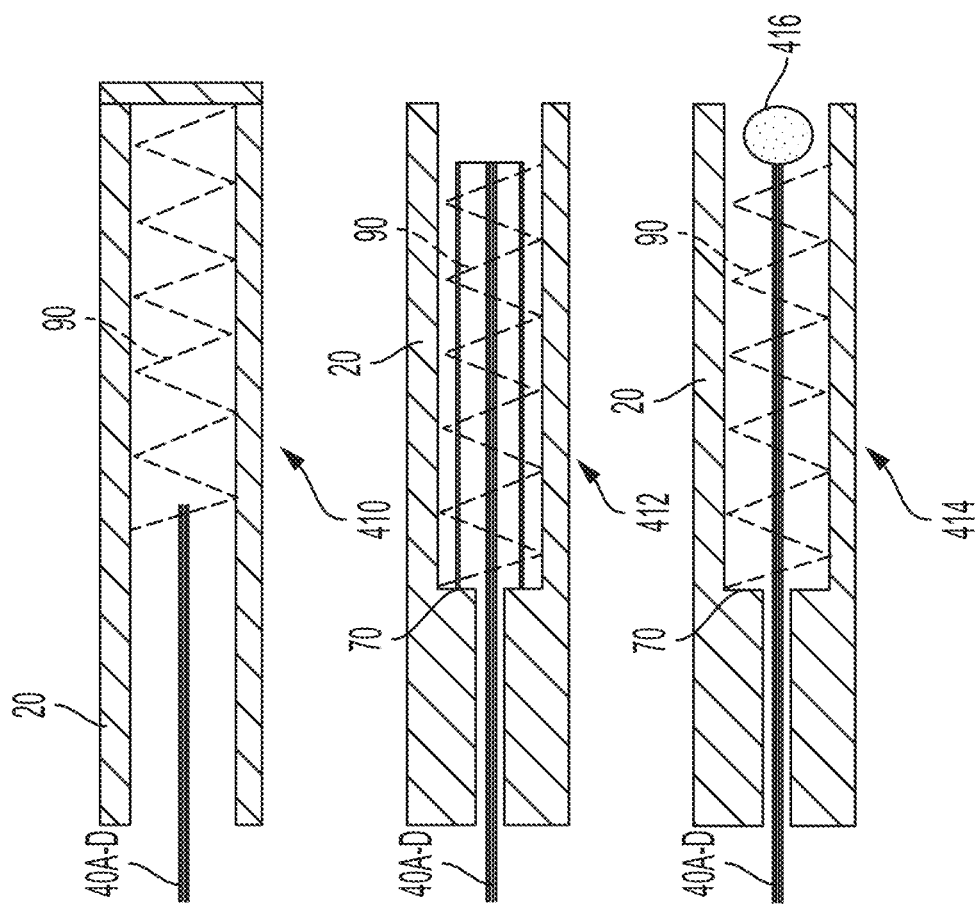

Referring to FIG. 4B, other alternative configurations of the tensioning tube, the resilient member, the resilient member stop, and/or the force applicator may be used. In some embodiments, the tension in the sutures may not be adjustable based on factors other than the resilient member spring force (e.g., as described below with respect to configurations 410, 412, and 414). In some other embodiments, the tension in the sutures may be adjustable based on other factors in addition to being dependent on the resilient member spring force (e.g., as described below with respect to configurations 420 and 422).

For example, configuration 410 can include a proximal end of the sutures 40A-D being directly coupled to or attached to a portion of resilient member 90 (e.g., close to or at the distal end), with the proximal end of the resilient member 90 being attached to a closed proximal end of tensioning tube 20. In such embodiments, a force applicator or a resilient member stop may not be provided. Rather, in such configuration 410, the resilient member 90 is configured to be put under a resilient force (e.g., in tension) by extension against the closed proximal end of the tensioning tube 20 compared to the resting state of the resilient member. For example, the suture length may be configured such that the resilient member is extended when the access site opening is expanded for insertion of an interventional device. The resilient member automatically returns to its resting state when the interventional device is removed thereby cinching the access site closed. Other non-adjustable configurations, such as configurations 412 and 414 can place resilient member 90 under compressive force when the access site opening is expanded for insertion of an interventional device. For example, in configuration 412, sutures 40A-D may extend axially through the center of resilient member 90, loop around the proximal ends of resilient member 90, then double back and attach to an inner surface of tensioning tube 20, for example, at resilient member stop 70. Thus, in configuration 412, when sutures 40A-D are pulled on at the distal end due to expansion of the access site opening, sutures 40A-D will cause compression of resilient member 90 against resilient member stop 70. The resilient member automatically returns to its resting state when the interventional device is removed thereby cinching the access site closed. It should be noted that in the configuration 416, a compression of the resilient member 90 by a distance "x" cause "2x" lengthening of the attached sutures. As another example configuration, configuration 414 can include a suture stop 416, such as a knot, ball, crimped stop, or other suitable member at the proximal end of the resilient member 90. In this configuration, the sutures 40A-D can extend axially through resilient member 90, with stop 416 contacting resilient member 90 and transferring tension in sutures 40A-D to resilient member 90 causing compression of the resilient member when the access site opening is expanded.

As discussed above, configurations 420 and 422 illustrate embodiments where the tension in the sutures is also dependent on factors additional to the spring force of the resilient member. For example, the tension in the sutures can be adjusted by moving the position of a force applicator 30 relative to sutures 40A-D within the tensioning tube 20, thus allowing more tension or less tension to be applied to sutures 40A-D by resilient member 90. In both configurations 420 and 422, sutures 40A-D can run axially through resilient member 90 and are coupled to a force applicator 30 that is moveable with respect to the sutures within the tensioning tube. For example, force applicator 30 can be a tube or ferrule that is crimped on to sutures 40A-D in a manner than permits sliding of force applicator 30 on sutures 40A-D. In the examples of FIGS. 4B, by sliding force applicator 30 to the left, a user may compress resilient member 90 and thus increase the tension placed on sutures 40A-D during use. For example, in some cases, additional cinching force may be required to fully stop bleeding (i.e., a force greater than that allowed by the resilient member itself), and a user may increase the suture tension via adjustment of the force applicator position with respect to the resilient member. Conversely, if force applicator 30 is slid to the right in FIG. 4B, force applicator 30 can expand and less tension can be placed on sutures 40A-D. In some embodiments, as shown by configuration 420, resilient member 90 may also be attached to force applicator 30. In other embodiments, as shown by configuration 422, force applicator 30 may not be attached to the resilient member 90. Thus, the user may employ the adjustability of the position of the force applicator with respect to the resilient member to further dynamically tune the cinching force based on a particular application (i.e., in addition to that provided by the resilient member). For example, a larger access site or larger vessel may require a larger cinching force (i.e., higher suture tension) to stop bleeding as opposed to a comparatively smaller access site or vessel.

In some embodiments, the resilient member 90 may be modular. For example, resilient member 90 may be removable from tensioning tube 20. Different strengths or sizes of resilient member 90 can then be interchanged within the system to provide tensioning for different applications. Resilient member 90 may also be modularly attached to a tensioning tube 20, in which sutures 40A-D are preinstalled. In yet another embodiment, the sutures may be fed into the tensioning system after of sutures are placed.

Optionally, when the access site is closed by cinching of the sutures 40A-D, a guide wire may continue to extend from the access site. When access into the vessel is desired, a new interventional device, may be placed over the guidewire and pushed into the opening. Optionally, a guidewire may not be present and the tensioning tube 20 may be used as a positioning tool for guiding an interventional device towards the access site.

In some example embodiments, the suture stop can be coupled to the proximal end of the force applicator member 30 and prevent the proximal end of the sutures 40A-D from sliding through force applicator member 30 beyond the stop. Thus, when the sutures around the access site are pulled apart, the suture stop will tension the sutures 40A-D, and cause compression (or extension) of the resilient member 90, via the force applicator 30. In some embodiments, the force applicator member 30 may comprise the suture stop. For example, the force applicator member 30 may be crimped or pinched at or near its proximal end, while the sutures 40A-D are inside. Such crimping can cause the force applicator member to grip onto the sutures and act as a suture stop. In further embodiments, the force applicator member may include a stop feature such as a hook or a thin notch, which could interface the sutures to fix the sutures to the resilient member. For example, the proximal end of the tubular wall of the force applicator member 30 may have a thin slit or notch cut into it angled relative to the main axis of the tube. The sutures 40A-D could be slide into this notch to inhibit their movement relative to the force applicator member 30. Similarly, force applicator member 30 can include a hook or other feature around which the sutures 40A-D could be wrapped or tied to fix them to the force applicator member 30.

One of ordinary skill will understand that the level of tension placed on the sutures 40 can be varied in several ways. The tension on the sutures 40 may be affected at least by the relative strength of the resilient member 90; spring constant of the resilient member 90 (i.e., if it is a spring); the relative lengths of the sutures 40A-D the tensioning tube 20, the resilient member 90, and the force applicator member 30; type of suture material (e.g., the amount the suture material will stretch); the location of the resilient member stop 70 within the tensioning tube 20; user adjustment of force applicator 30 (in adjustable tension configurations); or the like. In the various embodiments described herein, the tension placed on sutures 40A-D can fall within various ranges such as from 0.1 to 4 pounds, from 0.1 to 2 pounds, or from 0.25 pounds to 2 pounds or others. Required cinching force may depend up on the application. For example, a femoral artery will require different cinching force than a femoral vein because the pressure inside the vessels may be different.

Referring back to FIGS. 1-2, the distal end 22 of tensioning tube 20 may, optionally, include a suture lock 60. Suture lock 60 can hold the sutures 40A-D in tension to keep the access site permanently closed when additional access to the vessel lumen is no longer needed and the tensioning tube 20 has been removed. Additionally and/or alternatively, the suture lock may be placed onto the sutures 40A-D after the have been removed from the tensioning tube when additional access to the vessel lumen is no longer needed. Such permanent or semi-permanent closure can permit the access site to heal and prevent addition bleeding until healing is complete. As illustrated by FIG. 2, suture lock 60 can be a ferrule that slides over the sutures 40A-D. This ferrule can be crimped, causing it to be crushed around and grip the sutures, holding them in place. Optionally, the suture lock 60 may contact the tensioning tube 20, but can still be crimped while the tensioning tube is place, thus securing the sutures 40A-D in a tensioned position. After crimping of suture lock 60, the user could then cut the sutures 40A-D at the proximal end of the suture lock 60. This would then separate the anchors 50A-D, distal end of the sutures 40A-D, and suture lock 60 from the rest of the dynamic vascular access and closure device 10 and permanently close the access site.

Figure 6A:
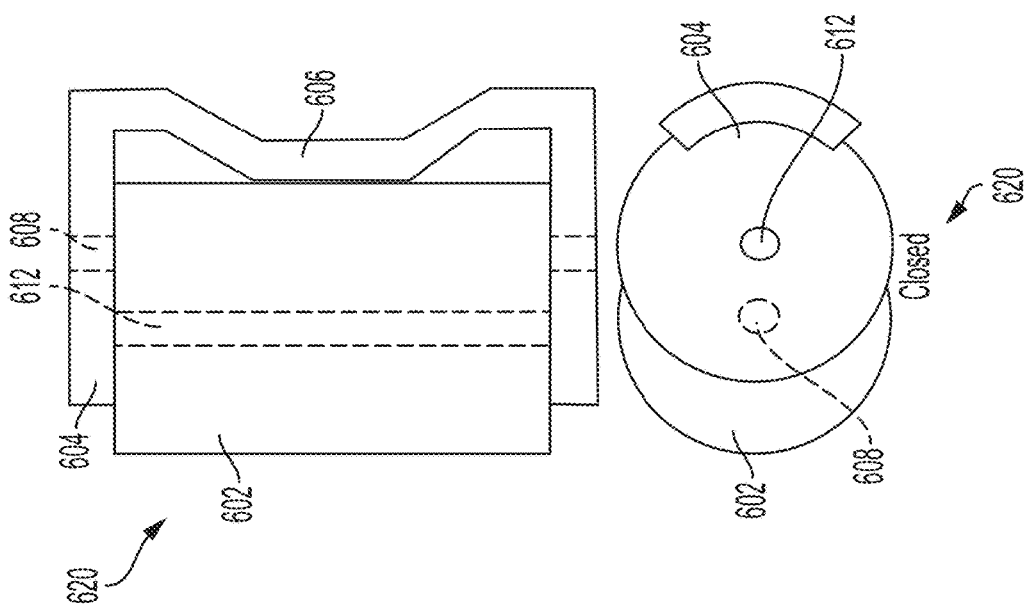
FIG. 6A illustrates an example of a semi-permanent suture lock.
Figure 6A:
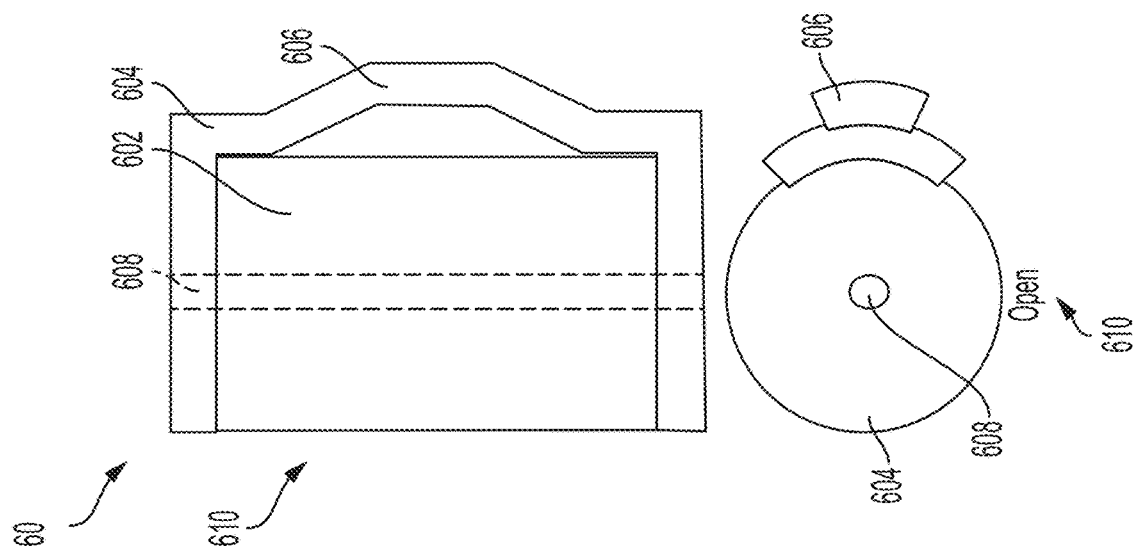

As described herein, suture lock 60 may take any now or hereafter existing form without deviating from the principles of this disclosure. One such example of a suture lock 60 is illustrated by FIG. 6A. FIG. 6A illustrates a selectable suture lock with an open position 600 and a closed position 620. As shown by the illustrated side and top views, the suture lock can include an inner body 602 and outer shell 604 disposed around inner body 602. Inner body 602 can be slideably connected to outer shell 604. Outer shell 604 may include a hole 608 extending through the top and bottom of outer shell 604. Inner body 602 can include a bore 612 that runs completely through inner body 602. In open position 600, holes 608 can be aligned coaxially with bore 612 to permit sutures to be placed through the suture lock. Outer shell can include a toggle 606 that can be used to displace inner body 602 relative to outer shell 604 to place the suture lock into closed position 620. When toggle 606 is pushed and moved transversely to the axis of bore 612, it can move inner body 602 transversely relative to outer shell 604. Thus, in closed position 620, holes 608 and bore 612 can be misaligned. The misalignment can trap sutures between inner body 608 and outer shell 612 to lock the sutures in place and prevent movement of the suture lock along the sutures.

Figure 6B:
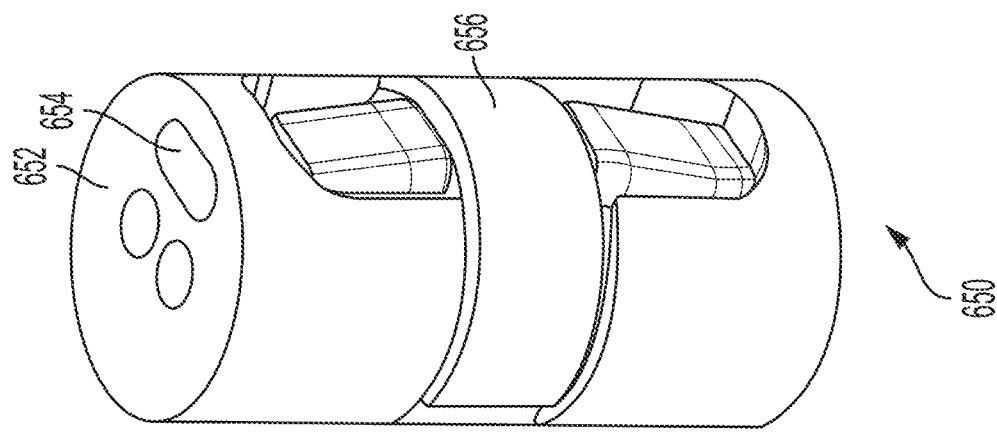
FIG. 6B illustrates additional exemplary semi-permanent suture locks.
Figure 6B:
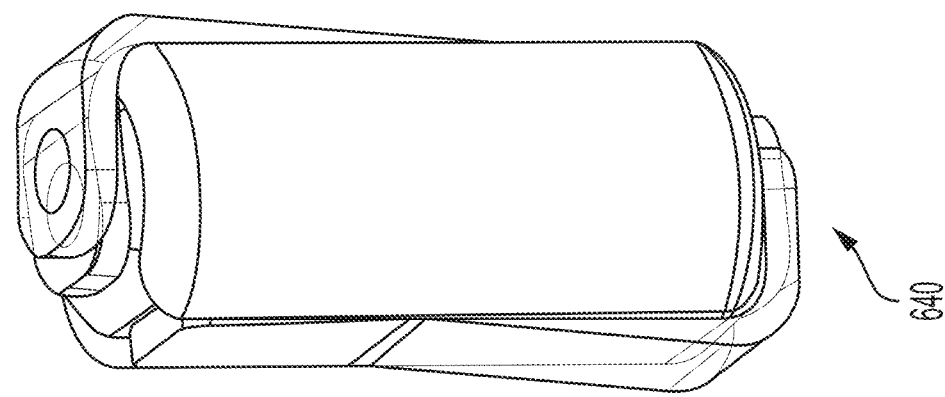
Figure 6B:
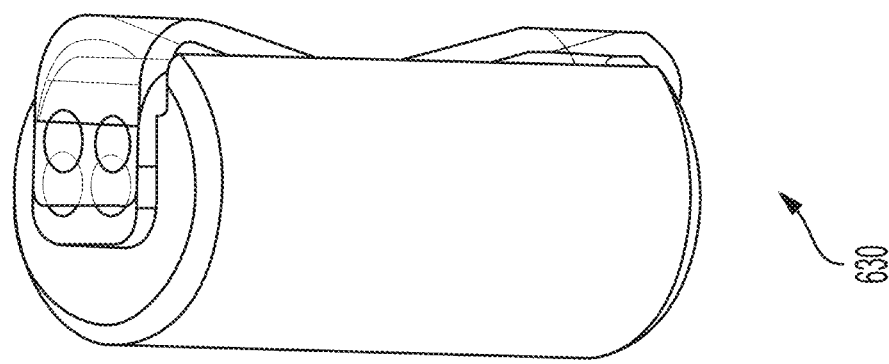

FIG. 6B illustrates other exemplary sutures locks. For example, suture locks 630 and 640 are a two-component selectable suture locks with two channels through which sutures may be extend. When the two-component lock is in a closed position, two locking members will pinch the suture and prevent the suture from slipping through the lock. In an open configuration, the channels are aligned and the sutures are free to move. When placed into a closed configuration, the channels can mal-aligned, preventing the sutures from moving freely. In some embodiments, in the event that the access site would need to be accessed again after the suture lock was tightened, the suture lock may be unlocked to permit free movement of the sutures. Lock 630 includes two separate bores for sutures, while lock 640 contains a single bore through which sutures can extend.

Lock 650 of FIG. 6B illustrates a 3 component suture lock design. Lock 650 includes a body 652 with two holes an open bore, the open bore can allow sutures to freely move through it. A stop element 654 that can be moved inside the channel to block the free movement of the sutures. The stop element can be moved from a closed position to an open position with toggle 656. While lock 650 is illustrated with two holes for sutures, more or fewer holes could be used.

Other types of suture locks are possible. For example, a suture lock could also take the form of a single body, single channel lock, for example, a ferrule made of metal which is crimped irreversibly at the end of the procedure to lock the distal end of sutures under tension.

FIG. 7 illustrates various example arrangements of suture placement on a blood vessel wall, consistent with disclosed embodiments. Examples 170, 180, and 190 show non-anchor based suture placement. As illustrated in FIG. 7, non-anchor based suture attachment may include a suture loop running inside the vessel. In the case of arrangement 170, a suture filament 172 may have entry/exit points 174, 176 spaced out transversely on the surface of the blood vessel. The distance between the points may vary based on, for example, the size of the vessel, the size of the suture, the size of the interventional device being introduced into the vessel lumen, etc. The suture may be looped through the vessel such that when the free ends of the suture outside of the vessel are pulled, the entry points of the suture are pulled together, thus closing the access site opening between the two entry points. Example 180 depicts a four point closure arrangement with two sutures. The two sutures 182, 184 can each have a transversely spaced entry/exit points. The two sutures can also be spaced axially along the vessel. For example, in arrangement 180, entry holes 186, 188 are axially spaced on the vessel. The transverse spacing between the entry/exit points of the two sutures may be substantially the same. Similarly, the axial spacing between the two sutures may be substantially the same as the transverse spacing between entries and exists, causing the four pulling points of the sutures to form a square on the vessel. Example arrangement 190 of FIG. 7 is a six point closure arrangement using three pieces of suture. Just as with arrangements having fewer points, the points of each suture can be transversely spaced apart. For example, entry points 192, 194 of the middle suture in arrangement 190 are transversely spaced. Additionally, the out sutures of arrangement 190 can be spaced along the main axis of the vessel. As shown in arrangement 190, even with greater than four points of attachment to the vessel, the tensioning tube 20 assembly can remain in the center of the points to ensure proper closure and substantially equal tension on each of the sutures. While the Figures generally depict symmetric arrangements of sutures, arrangements need not be symmetric. Additionally, while FIG. 7 illustrates arrangements having 2, 4, or 6 sutures, other numbers of sutures (including an odd number of sutures) can be used.

FIG. 7 also illustrates examples of anchor-based suture arrangements. For example, rather than using one piece of suture extending through the vessel and out of another point in the vessel, multiple pieces of suture can be used, each having an anchor disposed on the distal end. As described herein, the anchor can attach to the vessel wall. The sutures can then be pulled tight to draw the anchored ends together and close a vascular opening or access site. In an example arrangement 200, two sutures 202, 204 are used with anchors 206, 208, respectively. Anchors 206, 208 are placed on a transverse axis through the vessel and are spaced apart on that axis. Arrangement 210 uses four anchors 212, 214, 216, 218 spaced apart in a square pattern, with each anchor having its own attached suture. Similarly, arrangement 220 uses six anchors. In some embodiments, as shown in arrangement 220, arrangements may have more than four anchors, but still have a substantially square pattern. In this case, the spacing between corner anchors 222, 224, 226, 228 is substantially the same, creating a square, even though two additional anchors are disposed between anchors 222, 226 and anchors 224, 228. As noted above with respect to non-anchor suture patterns, having a symmetric pattern of anchors can permit the tensioning tube 20 assembly to be disposed in the center of the anchors to ensure proper closure and substantially equal tension on each of the sutures. Other suture arrangements and number of sutures (e.g., circular, star-shaped, etc.) are also within the scope of this disclosure.

The choice of suture arrangement may depend on, for example, the size of vessel being accessed and/or the size of the interventional instrument being used. Larger vessels and dilators may present a greater potential risk of bleeding to the patient. Smaller vessels may also have limited space to accept sutures or anchors, thus limiting the number or type of arrangement of sutures. As an example, a large catheter having a size of 24-30 French might require an arrangement of six anchors, such as 220. A smaller catheter, for example, a size of 12-24 French, may require less anchors, such as a four anchor arrangement 210. Even smaller catheters (e.g., those used in some arterial applications having a size of 6-12 French) might only require a linear two suture pattern, such as that of arrangement 200.

Figure 9:
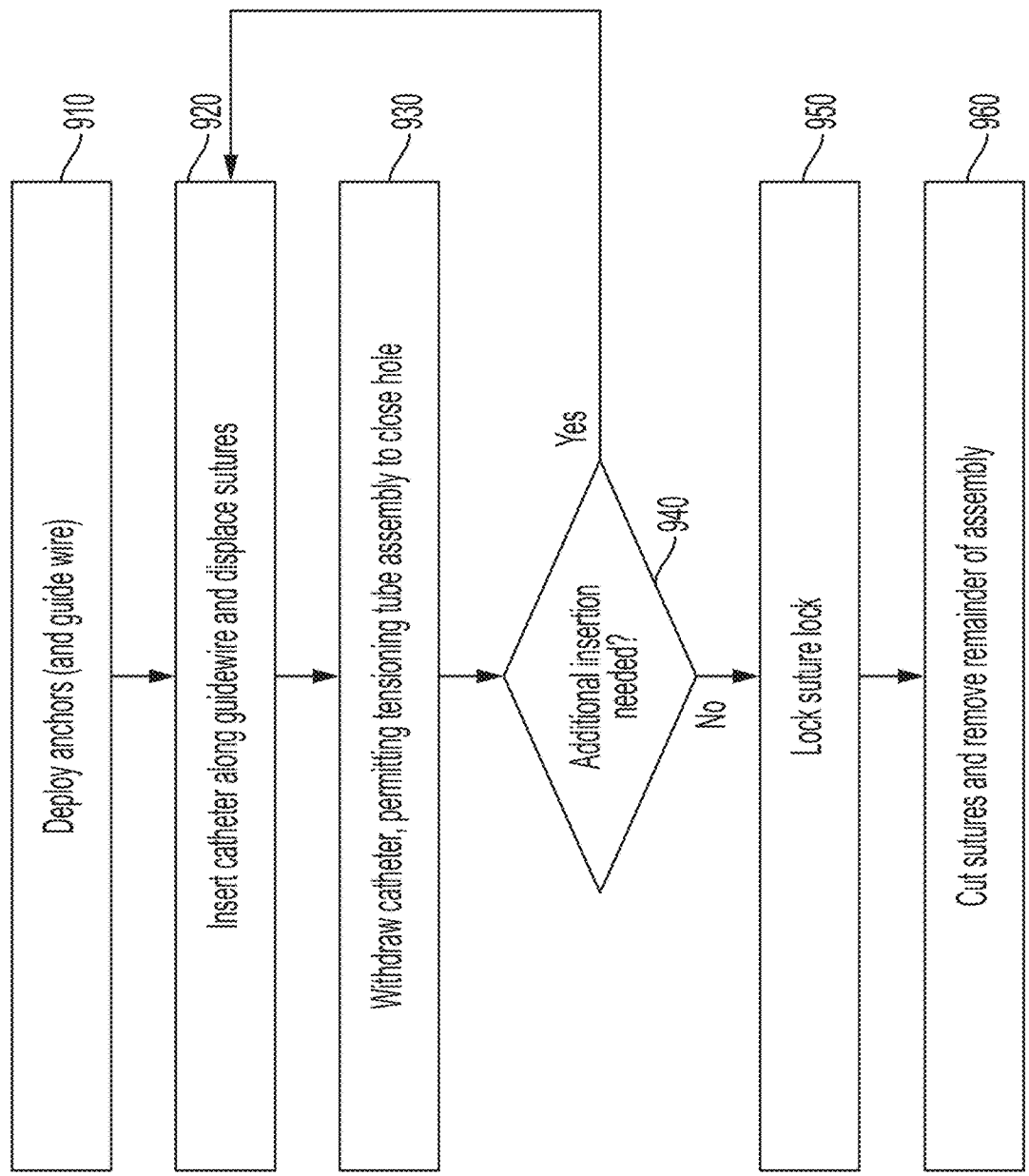
FIG. 9 is a flowchart illustrating an example method of using a dynamic vascular access and closure device.

FIG. 9 is a flowchart depicting an example method 900 for using a dynamic vascular access and closure device 10 of this disclosure. At step 910, the anchors and/or sutures may be deployed into the vessel wall using any now or hereafter known deployment devices. Step 910 may also include deploying of a guide wire. At this step, the dynamic vascular access and closure device can tension the sutures around the guidewire and/or an access site or hole in the vessel.

At step 920, method 900 may include inserting an interventional device over the guide wire into the vessel. In other embodiments, the sutures and tensioning device could be deployed before a vascular access. Accordingly, the anchors may be placed without a guidewire and the guidewire can be inserted after the placement of the device. As described herein, when the interventional device is inserted, the suture may be displaced or pulled, permitting the access site in the vessel to expand. The force applied to the sutures by the interventional device can cause a compression (or, in applicable embodiments, extension) of the resilient member within the tensioning tube. The force applied by the resilient member to the sutures will hold the anchors close to the instrument, sealing the vessel wall around the periphery of the instrument and preventing or reducing any unwanted bleeding. At step 930, the interventional device may be withdrawn from the vessel. As the instrument is withdrawn, the access hole will be closed by the sutures automatically as the resilient member is decompressed, which in turn can push on the suture stops and cause the sutures to cinch together. This automated closure of the access site can prevent bleeding when the interventional device is removed from the vessel. Such automated bleeding prevention is a significant improvement over the existing techniques because a user is not required to manually pinch the vessel to prevent the bleeding. Other times, a physician may need to employ a cross-over balloon, which can be balloon inserted from another access site and inflated temporarily to stop bleeding. The automated cinching provided by disclosed embodiments may mitigate the need for such a technique. Accordingly, through use of the dynamic vascular access and closure device, the procedure is made both easier for the surgeon and safer for the patient.

As described herein, the dynamic vascular access and closure device 10 of the disclosure also allows for reinsertion of an interventional device through the same access site. Accordingly, method 900 may include a determination at step 940 of whether an additional interventional device insertion is needed. If an additional interventional device insertion is needed, step 920 may be repeated. If an addition interventional device insertion is not need, step 950 may be executed. At step 950, the suture lock can be locked. As described herein, the suture lock may be locked by crimping a ferrule or locking a selectable lock, among other ways. At step 960, the sutures may be cut. The sutures maybe cut at any desired position, such as the distal end of the tensioning tube between the tensioning tube and the suture lock, leaving a relative minimum amount of extra suture attached to the patient's vessel. The tensioning tube assembly may be removed thereafter. In other embodiments, the suture could be cut at the proximal end of the resilient member, between the resilient member and the suture stop leaving a longer length of extra suture protruding from the suture lock (which may be used to tie a knot at the end of the suture lock to provide additional safety against unraveling of the sutures).

Figure 8:
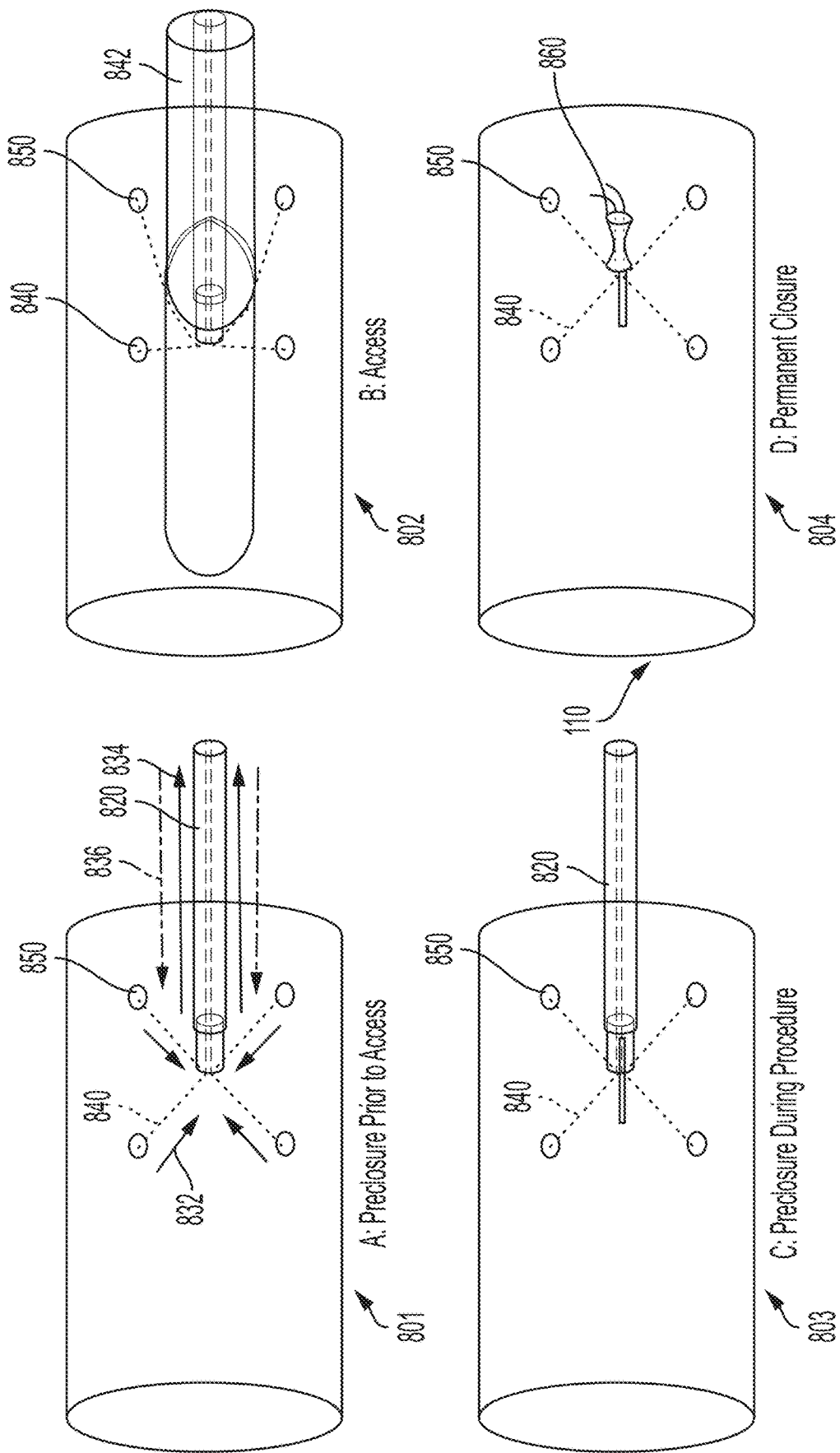
FIG. 8 is a schematic diagram illustrating an example method of using a dynamic vascular access and closure device.

FIG. 8 provides a visualization of the above process of using the dynamic vascular access and closure device 10 to provide access to a vessel lumen via an access site. The example in FIG. 8 shows four anchor-based sutures attached to a vessel around an access site 800. Illustration 801 shows the 4 sutures (collectively, 840) anchored in the vessel wall, via anchors (collectively, 850), while the access site 800 is cinched closed. The sutures 840 extend through a suture lock 860 and the tensioning tube 820 (including the components discussed above). Arrows 832 and 834 show the direction of cinching force applied by the sutures around the access site. As described above, this force can be a radial force drawing each of the anchors 850 toward the access site that is located between the anchors. Arrows 836 show the direction of the reaction force on the tensioning tube that pushes it towards the vessel wall. While FIG. 8 illustrates the anchors 850 being positioned in a substantially symmetrical configuration with respect to the access site, the disclosure is not so limiting, and the anchors can be placed in any suitable position. When the anchors are positioned in a substantially symmetric arrangement, and the sutures have approximately the same length, the tensioning tube 820 is centered between the anchors such that an approximately equal tension is applied in the sutures. In some embodiments, a guide wire (not illustrated) may be inserted into the access site 800 during anchor deployment. This guide wire may then be used to guide insertion of interventional devices into the access site. Optionally, a guidewire may not be present and the tensioning tube 820 may be used as a positioning tool for guiding an interventional device towards the access site (shown in 840).

Illustration 802 shows interventional device 842 as being inserted into the vessel lumen, via the access site 800. Insertion of the interventional device 842 into the access site 800, the access site 800 diameter increases causing pulling and tensioning of the sutures 840. As this occurs, the resilient member in the tensioning tube 820 is compressed to maintain tension in the sutures 840 such that the vessel wall closes around the interventional device 842 ensuring that there is no extraneous bleeding around the interventional device 842.

When the interventional device 842 is removed from the access site 800, the resilient member in the tensioning tube 820 will expand, pulling the sutures 840 towards one another to close the access site 800 (illustrated in 803). An interventional device (either the same one or a different one) may then be reinserted into the access site using the process shown in 802.

When the procedure is complete and access to the vessel lumen is no longer desired, the access site 800 may be closed more permanently using suture lock 860. As described herein, suture lock 880 may be crimped or otherwise locked. Then the sutures may then be cut, releasing the tensioning tube 820 assembly. Thus, as shown in illustration 804, the anchors 850, distal ends of the sutures 840, and the suture lock 880 remain to keep the vascular opening closed. If a guidewire was used during the procedure, it can also be removed before locking the suture lock 860.

It will be understood that terms such as "same," "equal," "planar," or "coplanar," as used herein when referring to orientation, layout, location, shapes, sizes, amounts, or other measures do not necessarily mean an exactly identical orientation, layout, location, shape, size, amount, or other measure, but are intended to encompass nearly identical orientation, layout, location, shapes, sizes, amounts, or other measures within acceptable variations that may occur, for example, due to manufacturing processes. The term "substantially" may be used herein to emphasize this meaning, unless the context or other statements clearly indicate otherwise. For example, items described as "substantially the same," "substantially equal," or "substantially planar," may be exactly the same, equal, or planar, or may be the same, equal, or planar within acceptable variations that may occur, for example, due to manufacturing processes and/or tolerances. The term "substantially" may be used to encompass this meaning, especially when such variations do not materially alter functionality.

It will be understood that various modifications may be made to the embodiments disclosed herein. Likewise, the above disclosed methods may be performed according to an alternate sequence. Therefore, the above description should not be construed as limiting, but merely as exemplification of the various embodiments. Those skilled in the art will envision other modifications within the scope and spirit of the claims appended hereto.

What is claimed is:

1. A method of cinching a vascular access site, the method comprising:
   attaching distal ends of a plurality of sutures at least partially around the vascular access site in a blood vessel, the sutures being attached to the blood vessel;
   advancing a tensioning tube over the plurality of sutures, the tensioning tube comprising a resilient member such that movement of the plurality of sutures causes compression or extension of the resilient member within the tensioning tube;
   inserting a medical device into the vascular access site;
   retracting the medical device from the access site, the retracting causing dynamic and reversible cinching of the vascular access site situated between the distal ends of the plurality of sutures by compression or extension of the resilient member within the tensioning tube; and
   reinserting the medical device into the vascular access site, wherein the reinsertion causes dynamic tensioning of the plurality of sutures to cinch the vascular access site around the medical device and prevent leakage.

2. The method of claim 1, wherein attaching the distal ends of the plurality of sutures at least partially around the vascular access site comprising attaching the distal ends via suture anchors.

3. The method of claim 1, further comprising tensioning the plurality of sutures to cinch the vascular access site around the medical device, wherein during inserting the medical device, the plurality of sutures are not tensioned.

4. The method of claim 3, wherein tensioning the plurality of sutures to cinch the vascular access site around the medical device comprises compressing or extending, via a force applicator disposed within the tensioning tube, the resilient member.

5. The method of claim 1, wherein at least one of the attaching, advancing, inserting, or retracting steps is performed percutaneously.

6. The method of claim 1, further comprising deploying a suture lock to irreversibly cinch the vascular access site in response to determining that no further insertion of a medical device into the vascular access site is desired.

7. The method of claim 1, wherein the resilient member is a spring.

8. The method of claim 1, the cinching is radial cinching.

9. The method of claim 1, wherein advancing a tensioning tube comprises advancing the tensioning tube such that the plurality of sutures extend axially between a distal end and a proximate end of the resilient member disposed within the tensioning tube.

10. The method of claim 9, further comprising deploying a suture stop proximate the proximal end of the resilient member such that a distance between the distal ends of the plurality of sutures and the suture stop remains constant.

11. The method of claim 9, further comprising looping the plurality of sutures outside the resilient member and deploying a suture stop proximate the distal end of the resilient member such that a distance between the distal ends of a plurality of sutures and the suture stop remains constant.

12. The method of claim 1, further comprising dynamically adjusting a tension in each of the plurality of sutures by adjusting a position of a force applicator with respect to the resilient member.

13. The method of claim 1, further comprising:
deploying a guidewire into the vascular access site;
attaching distal ends of the plurality of sutures at least partially around the guidewire access site; and
advancing the tensioning tube in proximity of the guidewire.

\* \* \* \* \*